US008454515B2

(12) United States Patent
Kamiyama et al.

(10) Patent No.: US 8,454,515 B2
(45) Date of Patent: Jun. 4, 2013

(54) ULTRASONIC DIAGNOSTIC APPARATUS AND ULTRASONIC DIAGNOSTIC METHOD

(75) Inventors: Naohisa Kamiyama, Otawara (JP); Tetsuya Yoshida, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 950 days.

(21) Appl. No.: 12/237,683

(22) Filed: Sep. 25, 2008

(65) Prior Publication Data

US 2009/0082670 A1 Mar. 26, 2009

(30) Foreign Application Priority Data

Sep. 26, 2007 (JP) ................................. 2007-249439

(51) Int. Cl.
*A61B 8/00* (2006.01)
*A61B 8/14* (2006.01)

(52) U.S. Cl.
USPC .......................................... 600/445; 600/444

(58) Field of Classification Search
USPC .......... 600/458, 445, 437, 443, 447, 453–457
See application file for complete search history.

(56) References Cited

U.S. PATENT DOCUMENTS

| | | | |
|---|---|---|---|
| 4,579,122 A * | 4/1986 | Shimizu et al. ............... | 600/445 |
| 5,694,937 A | 12/1997 | Kamiyama | |
| 5,944,666 A * | 8/1999 | Hossack et al. ............... | 600/458 |
| 2004/0073113 A1* | 4/2004 | Salgo et al. .................... | 600/438 |
| 2004/0102703 A1* | 5/2004 | Behren et al. ................. | 600/443 |
| 2004/0258127 A1* | 12/2004 | Ramamurthy et al. ....... | 374/117 |
| 2005/0059893 A1 | 3/2005 | Ogasawara et al. | |
| 2005/0203406 A1 | 9/2005 | Kamiyama | |
| 2006/0052699 A1* | 3/2006 | Angelsen et al. ............. | 600/437 |
| 2006/0116582 A1* | 6/2006 | Yoshida et al. ............... | 600/458 |

FOREIGN PATENT DOCUMENTS

| | | |
|---|---|---|
| JP | 8-196537 A | 8/1996 |
| JP | 11-155858 | 6/1999 |
| JP | 11-318890 | 11/1999 |
| JP | 11-318901 A | 11/1999 |
| JP | 2003-153900 A | 5/2003 |

(Continued)

OTHER PUBLICATIONS

U.S. Appl. No. 12/252,218, filed Oct. 21, 2008, Yoshida.

(Continued)

*Primary Examiner* — Sanjay Cattungal
*Assistant Examiner* — Lawrence Laryea
(74) *Attorney, Agent, or Firm* — Oblon, Spivak, McClelland, Maier & Neustadt, L.L.P.

(57) ABSTRACT

An ultrasonic diagnostic apparatus has a probe, an ultrasonic wave control unit, a volume data generation unit, and a three-dimensional display processing unit. The ultrasonic wave control unit controls the probe to transmit low-sound-pressure pulses to a scan region at a first pulse repetition period as well as controls the probe to receive an echo corresponding to the low-sound-pressure pulses. Further, the ultrasonic wave control unit controls the probe to transmit high-sound-pressure pulses to the scan region at a second pulse repetition period smaller than the first pulse repetition period. The volume data generation unit generates volume data based on the echo received by the probe under the control of the ultrasonic wave control unit. The three-dimensional display processing unit generates three-dimensional image data by performing a rendering process based on the volume data, and controls display of the three-dimensional image data on a monitor.

16 Claims, 8 Drawing Sheets

FOREIGN PATENT DOCUMENTS

| | | |
|---|---|---|
| JP | 2005-237738 | 9/2005 |
| JP | 2006-141798 | 6/2006 |
| JP | 2007-510451 | 4/2007 |
| WO | WO 01/01865 A1 | 1/2001 |
| WO | WO 2005/039418 A1 | 5/2005 |
| WO | WO 2005/044108 A1 | 5/2005 |

OTHER PUBLICATIONS

Japanese Office Action issued May 22, 2012 in Patent Application No. 2007-249439.

* cited by examiner

ULTRASONIC DIAGNOSTIC APPARATUS AND ULTRASONIC DIAGNOSTIC METHOD

BACKGROUND OF THE INVENTION

1. Field of the Invention

The present invention relates to a technology for transmitting low-sound-pressure pulses and high-sound-pressure pulses, which are ultrasonic pulses having a different sound pressure, respectively to a scan region which is formed so as to include a predetermined portion of an object to which a contrast agent bubble is injected, and for generating and displaying an ultrasonic image of the scan region based on an echo in correspondence to the low-sound-pressure pulse, and more particularly to an ultrasonic diagnostic apparatus and an ultrasonic diagnostic method for two-dimensionally or three-dimensionally displaying a minute blood flow of a blood capillary level and submitting a blood structure and hemodynamics as diagnosis information.

2. Description of the Related Art

In ultrasonic diagnosis, a beat of a heart and a moving behavior of a fetus can be displayed as a real-time display by a simple operation of applying an ultrasonic wave probe on a body surface as well as they can be repeatedly inspected since the ultrasonic diagnosis is excellent in safety. Since an ultrasonic diagnostic apparatus used for the ultrasonic diagnosis has a scale smaller than those of other diagnostic apparatuses such as an X-ray apparatus, a CT (computed tomography) apparatus, an MRI (magnetic resonance imaging) apparatus, and the like, the ultrasonic diagnostic apparatus can easily execute a clinical examination even if it is moved to a bed side. Further, a small-sized ultrasonic diagnostic apparatus such as an apparatus that can be carried by one hand is developed, although the ultrasonic diagnostic apparatus has various different sizes depending on the functions provided with it. Since the diagnosis using an ultrasonic wave is not adversely affected by exposure different from diagnosis making use of an X-ray and the like, it can be used in obstetrics, a home care, and the like.

Recently, since an intravenous-type ultrasonic contrast agent is commercially available, an "echo-image formation method" is being carried out. An object of the method is to intensify a blood flow signal by injecting an ultrasonic wave contrast agent from by a venous in the clinical examination of, for example, a heart, a liver, and the like and to estimate a hemodynamics. Many of contrast agents assume a microbubble as a reflection source. Since the bubble is a delicate base member, even if an ultrasonic wave is radiated in an ordinary diagnosis level, the bubble is broken by the mechanical action of the radiation with a result that the intensity of a signal from a scan surface is deteriorated. Accordingly, to observe the dynamic behavior of returned flow at a real time, it is necessary to relatively reduce the breakage of a bubble caused by the transmission of ultrasonic pulses by forming an image by transmitting low-sound-pressure ultrasonic pulses. When the low-sound-pressure ultrasonic pulses are transmitted, since a signal/noise ratio (S/N ratio) is also deteriorated when the image formed, various signal processing methods are devised to compensate the deterioration thereof.

Further, the following method is devised making use of the feature that the contrast agent bubble is broken. That is, the method (a) observes the dynamic behavior of bubbles which are filled on a scan surface by transmitting low-sound-pressure ultrasonic pulses; (b) breaks bubbles in the scan surface (strictly, in a radiated volume) by switching transmission of the low-sound-pressure ultrasonic pulses to transmission of a high-sound-pressure ultrasonic pulses; and (c) observes the behavior of the bubbles flowing in the scan surface by switching transmission of the high-sound-pressure ultrasonic pulses to transmission of the low-sound-pressure ultrasonic pulses. This method is called an FR (flash-replenishment) method (refer to, for example, Japanese Patent Application Publication No. 11-155858).

Incidentally, recently, since it becomes possible to display three-dimensional information by executing a three-dimensional scan at a real time, it is predicted that the FR method can be trially executed three-dimensionally. To execute a three-dimensional scan, there are two methods, that is, a method of using two-dimensional array probe in which piezoelectric vibrators are two-dimensionally disposed and a method of using a three-dimensional mechanical probe for mechanically sweeping one-dimensional arrays (including one and half dimensional arrays) disposed one-dimensionally.

When the FR method is expanded from two-dimension to three-dimension, it is preferable to instantly break all the bubbles in an interest region even if the FR method is executed three-dimensionally. However, when the FR method is executed using the mechanical probe for sweeping breakage of bubbles by radiating a high sound pressure, since a delay time occurs in a radiation region when the sweep is started and ended, there is a possibility that analysis of the reflow of bubbles is adversely affected and observation of the reflow is at initial timing thereof is omitted. Further, as an application of the FR method, there is a method of selectively breaking only the bubbles in a particular region (refer to, for example, Japanese Patent Application Publication No. 2005-237738). However, since transmission of a high sound pressure and transmission of a low-sound-pressure are alternately switched in a short time at the time, a sufficient time cannot be taken to the scan executed by transmitting the low-sound-pressure for observation.

When the FR method is expanded from two-dimension to three-dimension, it is preferable to instantly break all the bubbles in the interest region even if the FR method is executed three-dimensionally. However, when the FR method is executed by the mechanical probe for sweeping breakage of bubbles by radiating the high pressure sound, since a delay time occurs in a radiation region when the sweep is started and ended, there is a possibility that analysis of the reflow of contrast agent bubbles is adversely affected and observation at initial timing of the reflow is omitted. Further, as an application of the FR method, there is a method of selectively breaking only the bubbles in a particular region. However, since transmission of the high sound pressure and transmission of the low-sound-pressure are alternately switched in the short time at the time, a sufficient time cannot be taken to the scan executed by transmitting the low-sound-pressure for observation.

SUMMARY OF THE INVENTION

The present invention has taken into consideration the above-described problems, and it is an object of the present invention to provide an ultrasonic diagnostic apparatus of the present invention which can provide image information of a reflow of a contrast agent bubble desired by a user.

To solve the above-described problems, the present invention provides the ultrasonic diagnostic apparatus, comprising: an ultrasonic wave probe configured to transmit low-sound-pressure pulses and high-sound-pressure pulses having a different sound pressure to a scan region formed so as to include a predetermined portion of an object to which a contrast agent bubble is injected as well as receives an echo corresponding to the low-sound-pressure pulses; a low-sound-pressure ultrasonic wave transmission/reception control unit configured to control the ultrasonic wave probe to transmit the low-sound-pressure pulses to the scan region at a first pulse repetition period as well as to control the ultrasonic wave probe to receive the echo corresponding to the low-sound-pressure pulses; a high-sound-pressure ultrasonic wave transmission control unit configured to control the ultrasonic wave probe to transmit the high-sound-pressure pulses to the scan region at a second pulse repetition period smaller than the first pulse repetition period; a switching control unit configured to control the low-sound-pressure ultrasonic wave transmission/reception control unit and the high-sound-pressure ultrasonic wave transmission control unit so that the transmission of the low-sound-pressure pulses and the transmission of the high-sound-pressure pulses are alternately switched; a volume data generation unit configured to generate volume data based on the echo received by the ultrasonic wave probe under the control of the low-sound-pressure ultrasonic wave transmission/reception control unit; a three-dimensional display processing unit configured to generate three-dimensional image data by performing a rendering process based on the volume data; and a display control unit configured to control display of the three-dimensional image data on a monitor.

To solve the above-described problems, the present invention provides the ultrasonic diagnostic method, comprising: a high-sound-pressure ultrasonic wave transmission control step of controlling an ultrasonic wave probe to transmit high-sound-pressure pulses to a scan region at a first pulse repetition period smaller than a second pulse repetition period; a low-sound-pressure ultrasonic wave transmission/reception control step of controlling the ultrasonic wave probe to transmit low-sound-pressure pulses to the scan region at the second pulse repetition period as well as controlling the ultrasonic wave probe to receive an echo corresponding to the low-sound-pressure pulses; a volume data generation step of generating volume data based on the echo received by the ultrasonic wave probe under the control of the low-sound-pressure ultrasonic wave transmission/reception control step; a three-dimensional display processing step of generating three-dimensional image data by performing a rendering process based on the volume data; and a display control step of controlling display of the three-dimensional image data on a monitor.

DESCRIPTION OF THE PREFERRED EMBODIMENTS

An embodiment of an ultrasonic diagnostic apparatus and an ultrasonic diagnostic method according to the present invention will be explained referring to the accompanying drawings.

Figure 1:
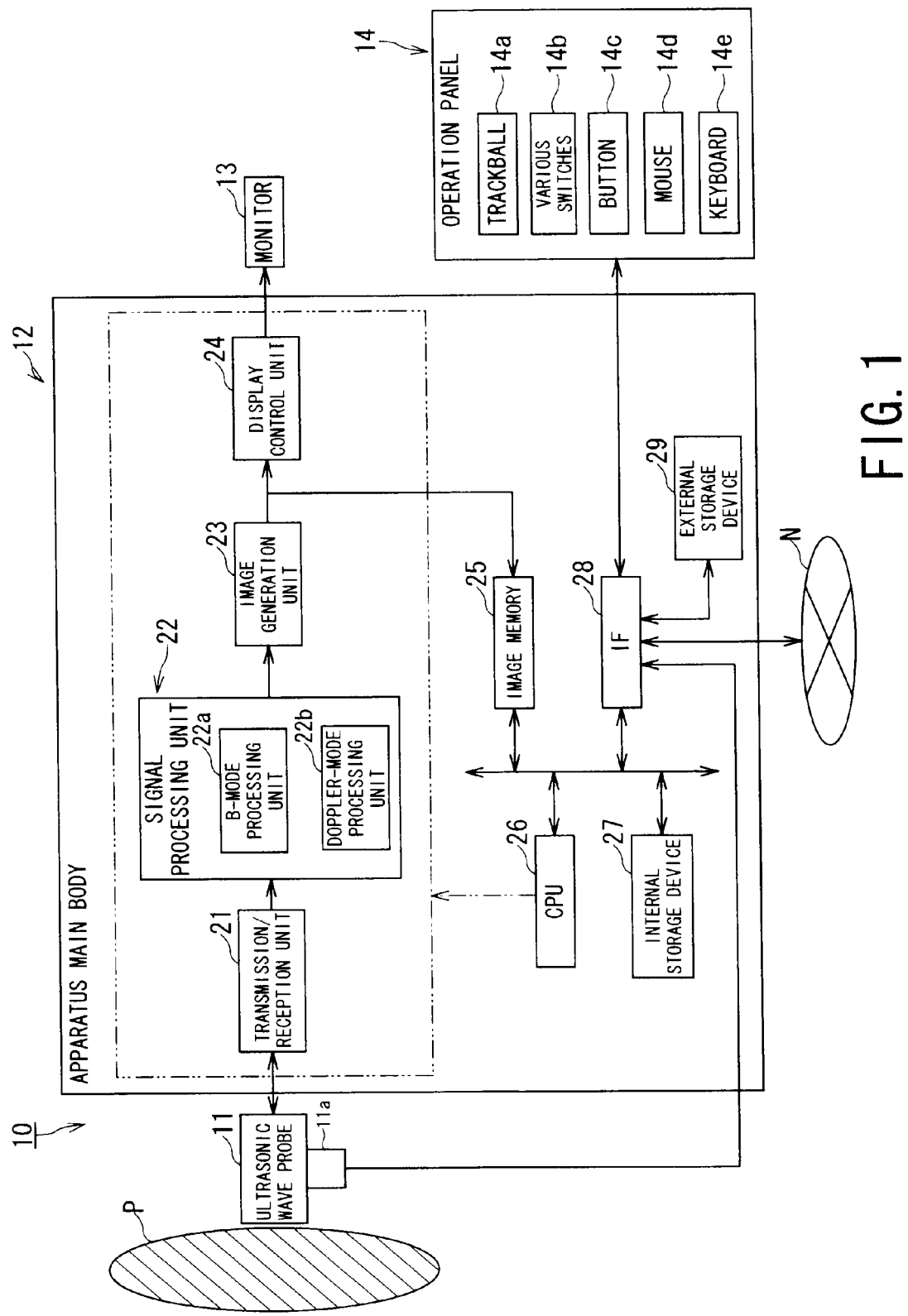
FIG. 1 is a block diagram showing the embodiment of the ultrasonic diagnostic apparatus according to the present invention.

FIG. 1 is a block diagram showing the embodiment of the ultrasonic diagnostic apparatus according to the present invention.

FIG. 1 shows an ultrasonic diagnostic apparatus 10 of a first embodiment. The ultrasonic diagnostic apparatus 10 mainly has an ultrasonic wave probe 11, an apparatus main body 12, a monitor 13 and an operation panel 14.

The ultrasonic wave probe 11 has a group of piezoelectric vibrators for transmitting ultrasonic pulses to a scan region including a predetermined portion of an object (patient) P based on drive pulses from the apparatus main body 12 as well as receiving an echo in correspondence to the transmitted ultrasonic pulses and converting it into an electric signal. When the ultrasonic pulses are transmitted from the group of the piezoelectric vibrators of the ultrasonic wave probe 11 to the scan region, an ultrasonic beam formed by the ultrasonic pulses is continuously reflected on the discontinuous surface of an acoustic impedance of an issue in the patient P. The piezoelectric vibrator group receives the reflected echo. The received echo is converted into an echo signal by the group of the piezoelectric vibrators. The amplitude of the echo signal depends on the difference between acoustic impedances on the discontinuous surface on which the echo reflects. Further, when the echo is reflected on a moving blood flow and the surface of a heart wall and the like, the echo in correspondence to the transmitted ultrasonic pulses is subjected to a frequency shift depending on the speed component a moving body in the direction in which an ultrasonic wave is transmitted Doppler effect.

Further, the ultrasonic wave probe 11 has a temperature measurement unit (thermistor) 11a for measuring the temperature of a piezoelectric vibrator in a transmission time zone in which high-sound-pressure pulses to be described later are transmitted.

For example, a one-dimensional probe, a one and half dimensional probe, a three-dimensional mechanical probe, and a two-dimensional probe (matrix array probe), and the like are exemplified as the ultrasonic wave probe 11. The one-dimensional probe is a probe in which a large number of (for example, 100 to 200 pieces of) piezoelectric vibrators are disposed only in an azimuth direction (X-axis direction). The one and half dimensional probe is a probe in which a large number of piezoelectric vibrators are disposed in the X-axis direction and a small number of (for example, three pieces of) piezoelectric vibrators are disposed in an elevational direction (Z-axis direction). The three-dimensional mechanical probe is a probe that can mechanically sweep a large number of piezoelectric vibrator groups disposed only in the X-axis direction or a probe that can mechanically sweep a large number of piezoelectric vibrator groups disposed in the X-axis direction and a small number of piezoelectric vibrator groups disposed in the Z-axis direction. Further, the two-dimensional probe is a probe in which a large number of piezoelectric vibrators are disposed in both the X-axis and Z-axis directions.

When the ultrasonic wave probe 11 is the one-dimensional probe, focusing is electronically executed by the large number of the piezoelectric vibrators disposed in the X-axis direction to form an appropriate ultrasonic beam extending in the Y-axis direction (depth direction) by converging the ultrasonic pulses in the X-axis direction. In contrast, when the ultrasonic wave probe 11 is the one-dimensional probe, it is preferable to dispose an acoustic lens to one piezoelectric vibrator on the ultrasonic wave radiation side thereof in the Z-axis direction and to arrange the piezoelectric vibrator as a concave vibrator to form an appropriate ultrasonic beam extending in the Y-axis direction by converging the ultrasonic pulses in the Z-axis direction.

When the ultrasonic wave probe 11 is the one and half dimensional probe, focusing is electronically performed by a large number of piezoelectric vibrators disposed in the X-axis direction to form an appropriate ultrasonic beam extending in the Y-axis direction by converging the ultrasonic pulses in the X-axis direction. In contrast, when the ultrasonic wave probe 11 is the one and half dimensional probe, the acoustic lens is disposed to a small number of piezoelectric vibrators on the ultrasonic wave radiation side thereof in the Z-axis direction and the number of the piezoelectric vibrators to be driven in the small number of the piezoelectric vibrators is changed according to the position of a focus in the Y-axis direction to form an appropriate ultrasonic beam extending in the Y-axis direction by converging the ultrasonic pulses in the Z-axis direction.

When the ultrasonic wave probe 11 is a three-dimensional mechanical probe, focusing is electronically performed by a large number of the piezoelectric vibrators disposed in the X-axis direction to form an appropriate ultrasonic beam extending in the Y-axis direction by converging the ultrasonic pulses in the X-axis direction. In contrast, when the ultrasonic wave probe 11 is a three-dimensional mechanical probe, it is preferable to dispose an acoustic lens to one piezoelectric vibrator on the ultrasonic wave radiation side thereof in the Z-axis direction and to arrange the piezoelectric vibrator as a concave vibrator to form an appropriate ultrasonic beam extending in the Y-axis direction by converging the ultrasonic pulses in the Z-axis direction. Further, when the ultrasonic wave probe 11 is the three-dimensional mechanical probe, the acoustic lens is disposed to a small number of piezoelectric vibrators on the ultrasonic wave radiation side thereof in the Z-axis direction to form an appropriate ultrasonic beam extending in the Y-axis direction by converging the ultrasonic pulses in the Z-axis direction. Alternatively, when a three-dimensional region is scanned using the three-dimensional mechanical probe, a plurality of two dimensional cross sections (X-Y cross sections) are scanned by the ultrasonic beam formed by the ultrasonic pulses while sweeping the group of the piezoelectric vibrators.

When the ultrasonic wave probe 11 is the two-dimensional probe, focusing is electronically performed by a large number of piezoelectric vibrators disposed in the X-axis and Z-axis directions to form an appropriate ultrasonic beam extending in the Y-axis direction by converging the ultrasonic pulses in the X-axis and Z-axis directions. When a three-dimensional region is scanned using the two-dimensional probe, a plurality of X-Y cross sections are scanned by the ultrasonic beam formed by the ultrasonic pulses while electronically shifting the transmission surfaces of the ultrasonic pulses in the Z-axis direction.

Although a case, in which the ultrasonic wave probe 11 is the three-dimensional mechanical probe, will be explained below as an example, the ultrasonic wave probe 11 may be the two-dimensional probe and the like.

The apparatus main body 12 has a transmission/reception unit 21, a signal processing unit 22, an image generation unit 23, a display control unit 24, an image memory 25, a CPU (central processing unit) 26, an internal storage device 27, an IF 28, and an external storage device 29. Note that although it is explained that the transmission/reception unit 21, the signal processing unit 22, the image generation unit 23, and the display control unit 24 are composed of hardware such as an integrated circuit and the like in the embodiment, all or a part of them may be functioned by executing a software program arranged as modules.

The transmission/reception unit 21 has a transmission unit and a reception unit each not shown. The transmission unit has a not shown pulser unit, a transmission delay unit, a trigger generation unit, and the like. The pulser unit repeatedly generates rate pulses for forming an ultrasonic wave for transmission at a predetermined rate frequency fr [Hz] (cycle; 1/fr second). Further, in the transmission delay unit, an ultrasonic wave of each channel is converged like a beam as well as a delay time is necessary to determine transmission directionality is given to each rate pulse. The trigger generation unit applies the drive pulses to the piezoelectric vibrator of the ultrasonic wave probe 11 at timing based on a rate pulse.

Note that a transmission unit of the transmission/reception unit 21 has a function capable of instantly changing a transmission frequency, a transmission drive voltage (sound pressure), a transmission pulse rate, a scan region, the number of times of flash, and the like according to the instruction of the CPU 26. In particular, the sound pressure can be changed by a linear amplifier type transmission unit capable of instantly switching the value thereof or a mechanism for electrically switching a plurality of power supplies.

Figure 2:
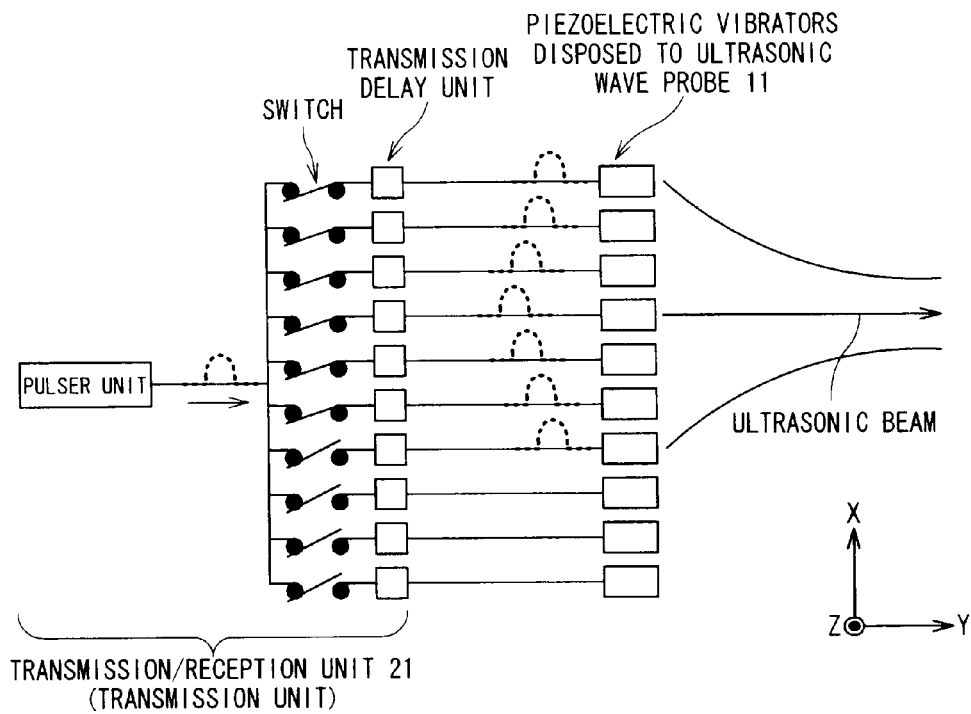
FIG. 2 is a view explaining a flow of pulses in an ultrasonic wave probe and a transmission/reception unit.

FIG. 2 is a view explaining a flow of pulses in the ultrasonic wave probe 11 and the transmission/reception unit 21.

FIG. 2 shows the transmission/reception unit 21 shown in FIG. 1, a large number of piezoelectric vibrators disposed to the ultrasonic wave probe 11 in the X-axis direction, and an ultrasonic beam formed by the ultrasonic pulses transmitted from the piezoelectric vibrators in the Y-axis direction. The ultrasonic beam is formed by giving a necessary delay time by a transmission delay unit of each channel to the rate pulse generated by the pulser unit included in the transmission/reception unit 21.

Further, a reception unit of the transmission/reception unit 21 shown in FIG. 1 has a not shown amplifier, a reception delay unit, an A/D (analog to digital) converter, an addition unit, and the like. The amplifier amplifies the echo signal of each channel fetched through the ultrasonic wave probe 11.

The reception delay unit gives the delay time necessary to determine reception directionality to the echo signal amplified by the amplifier. The A/D converter converts the echo signal output from the reception delay unit into a digital signal. The addition unit executes an addition process to the digital echo signal. A reflection component from the direction according to the reception directionality of the echo signal is emphasized by the addition executed by the addition unit, thereby an integral beam for transmitting and receiving an ultrasonic wave is formed by reception directionality and transmission directionality.

The signal processing unit 22 has a B-mode processing unit 22a and a doppler-mode processing unit 22b.

The B-mode processing unit 22a performs a logarithm amplification process, an envelope detection process, and the like to the echo signal output from the reception unit of the transmission/reception unit 21, and generates data in which signal intensity is expressed by the brightness of luminance. The data is transmitted to the image generation unit 23 and displayed on the monitor 13 as a B-mode image in which the intensity of a reflected wave is expressed by the luminance through the display control unit 24.

The doppler-mode processing unit 22b analyzes the frequency of speed information from the echo signal output from the reception unit of the transmission/reception unit 21, extracts a blood flow, a tissue, and a contrast agent echo component by Doppler effect and obtains blood flow information such as an average speed, dispersion, power, and the like as a multiplicity of points. The blood flow information is sent to the image generation unit 23 and displayed on the monitor 13 in color through the display control unit 24 as an average speed image, a dispersion image, a power image and a combination image of them.

The image generation unit 23 converts a scan line signal train obtained by an ultrasonic wave scan into a scan line signal train of an ordinary video format represented by a television and the like and generates the image data of an ultrasonic image as a display image.

The display control unit 24 generates data for display based on the two dimensional image data output from the image generation unit 23 and the three-dimensional image data output from the CPU 26 and performs an analog conversion to the data. Further, the display control unit 24 synthesizes image data together with character information, a scale, and the like of various parameters and outputs the image data to the monitor 13 as a video signal.

The image memory 25 is a storage memory for storing the image data of the ultrasonic image output from the image generation unit 23. The image data stored in the image memory 25 can be called out by a user, for example, after diagnosis is performed and can be reproduced as a still image or a motion image using a plurality of still images.

The CPU 26 has a function as an information processing apparatus (calculator) and controls the operation of the apparatus main body 12 in its entirety. The CPU 26 executes a program stored in the internal storage device 27. Otherwise, the CPU 26 loads a program stored in the external storage device 29 and a program transferred from a network N, received by the IF 28, and installed on the external storage device 29 and executes the programs.

The internal storage device 27 is a memory unit which also acts as elements such as a ROM (read only memory), a RAM (random access memory), and the like, stores IPL (initial program loading), BIOS (basic input/output system), and temporarily stores the work memory and the data of the CPU 26.

The IF 28 is an interface as to the input apparatus 13, the network N such as a hospital backbone LAN (local area network) and the like, the external storage device 29, the operation panel 14, and the like. The data such as the ultrasonic image and the like obtained by the apparatus main body 12, a result of analysis, and the like can be transferred by the IF 28 to other apparatus through the network N.

The external storage device 29 is an HD (hard disk) composed of metal to which, for example, a magnetic material is coated or vapor deposited, and data can be read and written by the HD (hard disk drive) arranged integrally with the HD. The external storage device 29 is a memory unit for storing the program (including OS (operating system) and the like in addition to a program (application program) installed on the apparatus main body 12. Further, the OS uses many graphics to display information to the user and can provide GUI (graphical user interface) which can execute a basic operation by the input unit 13.

The internal storage device 27 or the external storage device 29 stores a control program of the ultrasonic diagnostic apparatus 10, diagnosis information (patient ID (identification), findings of a doctor, and the like), a diagnosis protocol, transmission/reception conditions, and other data group. The internal storage device 27 or the external storage device 29 is also used to store the image data temporarily stored in the image memory 25 when necessary. Further, the data stored in the internal storage device 27 or the external storage device 29 can be also transferred to the network N through the IF 28.

The monitor 13 displays two-dimensional image data and three-dimensional image data together with the character information, the scale, and the like of various parameters based on the video signal from the display control unit 24.

The operation panel 14 is connected to the apparatus main body 12 and has a trackball 14a, various switches 14b, a button 14c, a mouse 14d, a keyboard 14e, and the like for fetching various instructions from the user (operator), an instruction for setting a region of interest (ROI), an instruction for setting various image quality conditions, and the like to the apparatus main body 12. The user can inputs the transmission frequency of the ultrasonic pulses transmitted from the ultrasonic wave probe 11, a transmission drive voltage (sound pressure), a transmission pulse rate, a scan region, the number of times of flash, reception conditions, and the like to the apparatus main body 12 through the operation panel 14.

Figure 3:
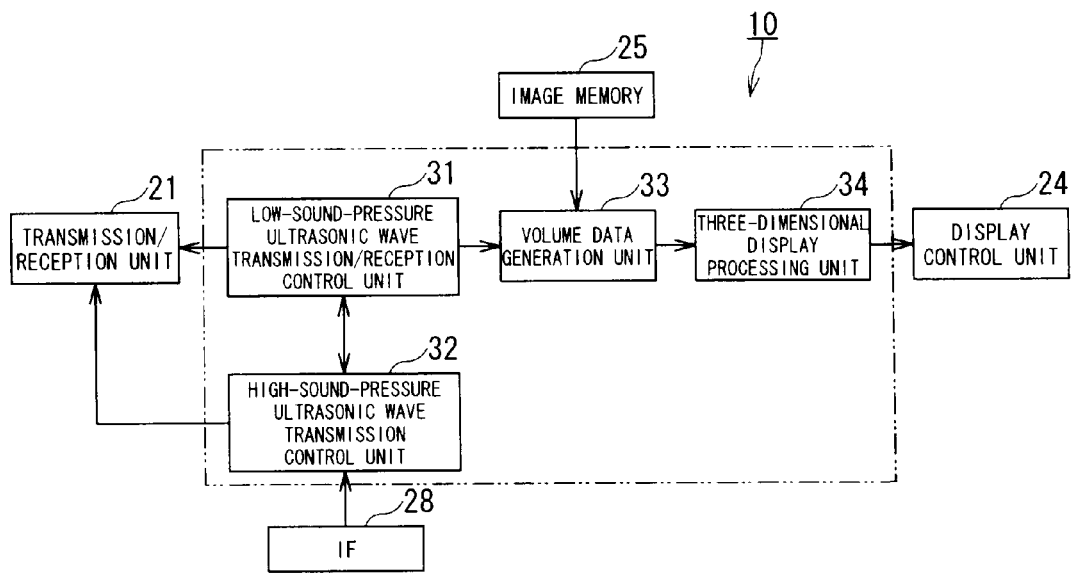
FIG. 3 is a block diagram showing a function of the embodiment of the ultrasonic diagnostic apparatus.

FIG. 3 is a block diagram showing a function of the embodiment of the ultrasonic diagnostic apparatus 10.

The ultrasonic diagnostic apparatus 10 is provided with a low-sound-pressure ultrasonic wave transmission/reception control unit 31, a high-sound-pressure ultrasonic wave transmission control unit 32, a volume data generation unit 33, and a three-dimensional display processing unit 34 by that the CPU 26 shown in FIG. 1 executes a program. Note that, in the embodiment, although it is explained that the low-sound-pressure ultrasonic wave transmission/reception control unit 31, the high-sound-pressure ultrasonic wave transmission control unit 32, the volume data generation unit 33, and the three-dimensional display processing unit 34 function by executing the software program arranged as the modules, all or a part them may be composed of hardware such as integrated units and the like.

The low-sound-pressure ultrasonic wave transmission/reception control unit 31 has a function for controlling the transmission/reception unit 21 so that it transmits low-sound-pressure ultrasonic pulses (hereinafter, called "low-sound-pressure pulses"), which have such a degree that they do not relatively break a contrast agent bubble in an arbitrary pulse repetition period (PRP) as well as controlling the transmission/reception unit 21 so that it receives an echo in correspondence to the low-sound-pressure pulses. A returned blood flow before the contrast agent bubble is broken can be made to an image at a real time in response to the echo signal received by the transmission/reception unit 21 under the control of the low-sound-pressure ultrasonic wave transmission/reception control unit 31. Note that the PRP is an inverse number of a pulse repetition frequency (PRF) of an ultrasonic wave.

The high-sound-pressure ultrasonic wave transmission control unit 32 has a function for controlling the transmission/reception unit 21 so that it transmits high-sound-pressure ultrasonic pulses (hereinafter, called "high-sound-pressure pulses"), which have such a degree that they break the contrast agent bubble at arbitrary timing to the scan region by the PRP smaller than that of the low-sound-pressure pulses. That is, the high-sound-pressure ultrasonic wave transmission control unit 32 repeatedly transmits the high-sound-pressure pulses at arbitrary timing by the PRP smaller than that of the low-sound-pressure pulses and executes a control so that flash is uniformly performed to the entire scan region as a three-dimensional region.

Here, two cases are exemplified as an object for breaking the contrast agent bubble by the high-sound-pressure pulses. One of them is a case in which it is necessary to form an image of the returned blood flow when the contrast agent bubble is broken. The other of them is a case in which it is not necessary to form the image of the returned blood flow when the contrast agent bubble is broken. Since the high-sound-pressure ultrasonic wave transmission control unit 32 has the latter object, it is not necessary for the high-sound-pressure ultrasonic wave transmission control unit 32 to receive the echo in correspondence to the high-sound-pressure pulses. Accordingly, the high-sound-pressure ultrasonic wave transmission control unit 32 can make the PRP extremely smaller than the PRP by the low-sound-pressure ultrasonic wave transmission/reception control unit 31.

Figure 4:
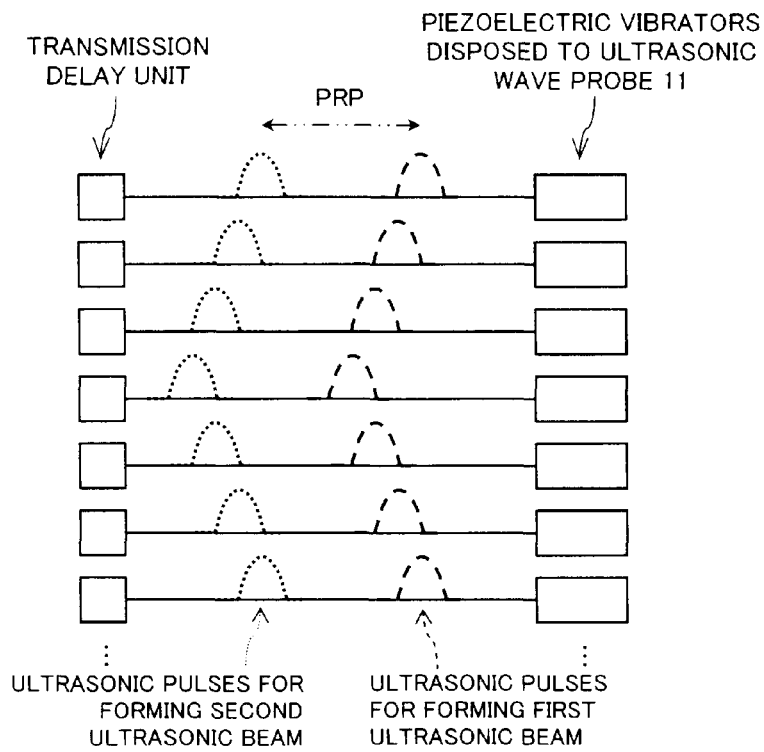
FIG. 4 is a view showing a first example of a PRP of high-sound-pressure pulses.
Figure 5:
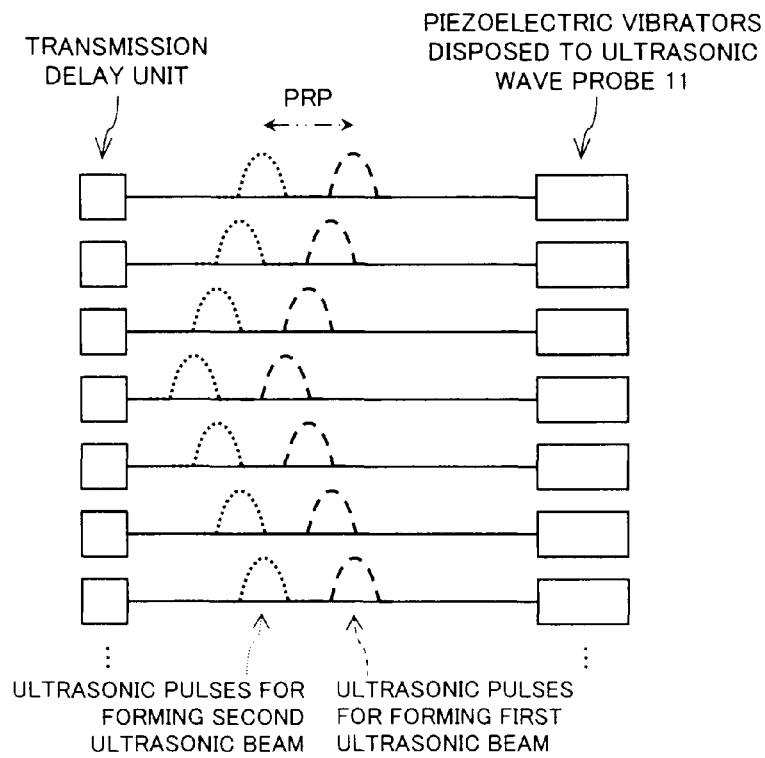
FIG. 5 is a view showing a second example of a PRP of high-sound-pressure pulses.

FIG. 4 is a view showing a first example of the PRP of the high-sound-pressure pulses controlled by the high-sound-pressure ultrasonic wave transmission control unit 32 and shows the PRP when ultrasonic pulses for forming a second ultrasonic beam are transmitted after all the ultrasonic pulses for forming a first ultrasonic beam is transmitted. FIG. 5 is a view showing a second example of the PRP of the high-sound-pressure pulses controlled by the high-sound-pressure ultrasonic wave transmission control unit 32 and shows the PRP when ultrasonic pulses for forming the second ultrasonic beam are transmitted while the ultrasonic pulses for forming the first ultrasonic beam are being transmitted.

When it is necessary to electronically focus the high-sound-pressure pulses, a delay time is necessary for transmission focusing as explained using FIG. 2. For example, when the three-dimensional mechanical probe is used as the ultrasonic wave probe 11, the group of the piezoelectric vibrators must be electronically focused in the X-axis direction. Accordingly, in a case shown in FIG. 4, the lower limit of the PRP is restricted by a delay time necessary to the transmission focusing in the X-axis direction. Note that it is preferable to set the PRP of the high-sound-pressure pulses approximately to the delay time necessary to the transmission focusing in the X-axis direction. Further, the group of the piezoelectric vibrators is swept to scan the three-dimensional region when the three-dimensional mechanical probe is used. In this case, since an echo receiving time can be omitted when the high-sound-pressure pulses are transmitted by the high-sound-pressure ultrasonic wave transmission control unit 32, the sweep speed when the high-sound-pressure pulses are transmitted can be made larger than that when the low-sound-pressure pulses are transmitted.

Further, when the two-dimensional probe is still used as the ultrasonic wave probe 11, the group of the piezoelectric vibrators must be electronically focused in the X-axis and Z-axis directions. Accordingly, in the case shown in FIG. 4, the lower limit of the PRP is restricted by a delay time necessary to the transmission focusing in the X-axis and Z-axis directions. Note that it is preferable to set the PRP of the high-sound-pressure pulses approximately to the delay time necessary to the transmission focusing in the X-axis and Z-axis directions.

In contrast, it is necessary to electronically focus the high-sound-pressure pulses, the lower limit of the PRP is not restricted and preferably as small as possible according to the second example of the PRP of the high-sound-pressure pulses shown in FIG. 5.

Further, when the temperature measured by a temperature measurement unit 11a exceeds a preset threshold value, the high-sound-pressure ultrasonic wave transmission control unit 32 shown in FIG. 3 may control the ultrasonic wave probe 11 so as to finish the transmission of the high-sound-pressure pulses based on the data of the temperature of the piezoelectric vibrators of the ultrasonic wave probe 11 from the temperature measurement unit 11a through the IF 28. A smaller PRP of the high-sound-pressure pulses, that is, a higher PRF of the high-sound-pressure pulses causes the temperature of the piezoelectric vibrators to more increase. To suppress the increase of the temperature, the transmission itself of the high-sound-pressure pulses is finished according to the measured temperature of the piezoelectric vibrators without regulating the sound pressure by adjusting a voltage to the piezoelectric vibrators. With this operation, when the high-sound-pressure pulses are transmitted in a short time, the pulses can be transmitted at the maximum sound pressure which can be used in the PRP used in an ordinary scan or at a sound pressure larger than it.

Further, the high-sound-pressure ultrasonic wave transmission control unit 32 can effectively reduce a flash time necessary to perform flash once the entire scan region while also roughing the intervals between high-sound-pressure beams for the purpose of reducing the transmission time of the high-sound-pressure pulses by the high-sound-pressure ultrasonic wave transmission control unit 32.

Note that the scan region of the ultrasonic beam (hereinafter, called "high-sound-pressure beam") which is formed by the high-sound-pressure pulses under the control of the high-sound-pressure ultrasonic wave transmission control unit 32 may be the same as the scan region of the ultrasonic beam (hereinafter, called "low-sound-pressure beam") which is formed by the low-sound-pressure pulses under the control of the low-sound-pressure ultrasonic wave transmission/reception control unit 31, and the scan region of the high-sound-pressure beam may be different from the scan region of the low-sound-pressure beam. When the scan region of the high-sound-pressure beam is different form the scan region of the low-sound-pressure beam, the scan region of the high-sound-pressure beam is wider than the scan region of the low-sound-pressure beam or the scan region of the high-sound-pressure beam is narrower than the scan region of the low-sound-pressure beam.

Figure 6:
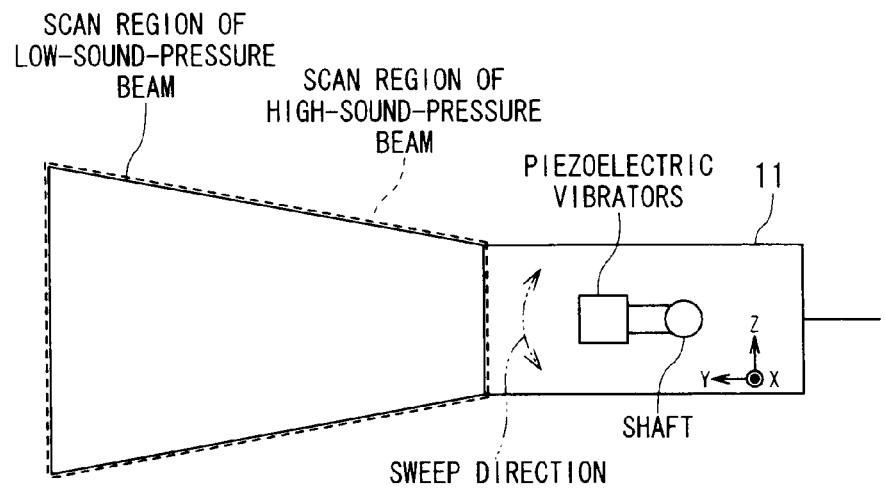
FIG. 6 is a schematic view showing a scan region of a low-sound-pressure beam and a scan region of a high-sound-pressure beam.
Figure 7:
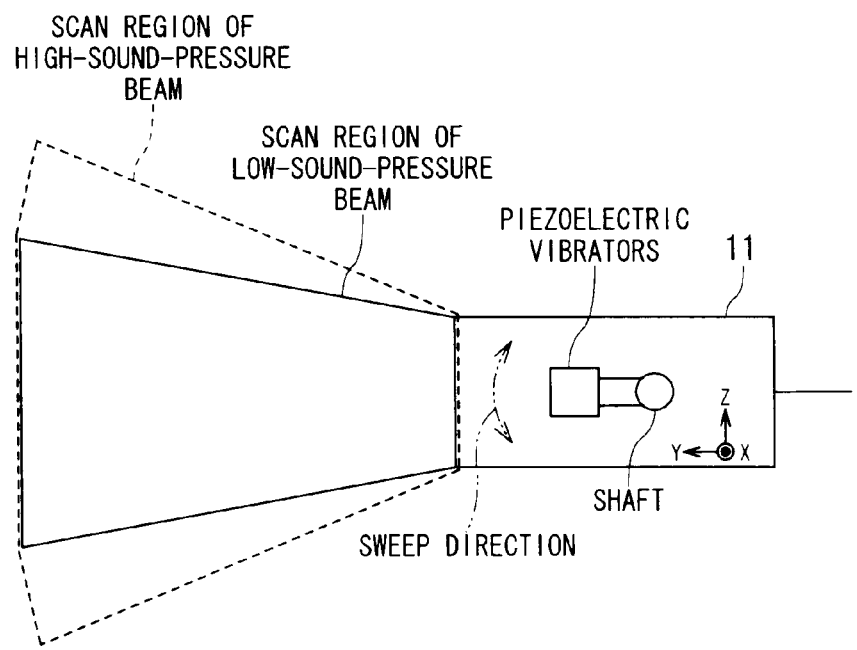
FIG. 7 is a schematic view showing a scan region of a low-sound-pressure beam and a scan region of a high-sound-pressure beam.
Figure 8:
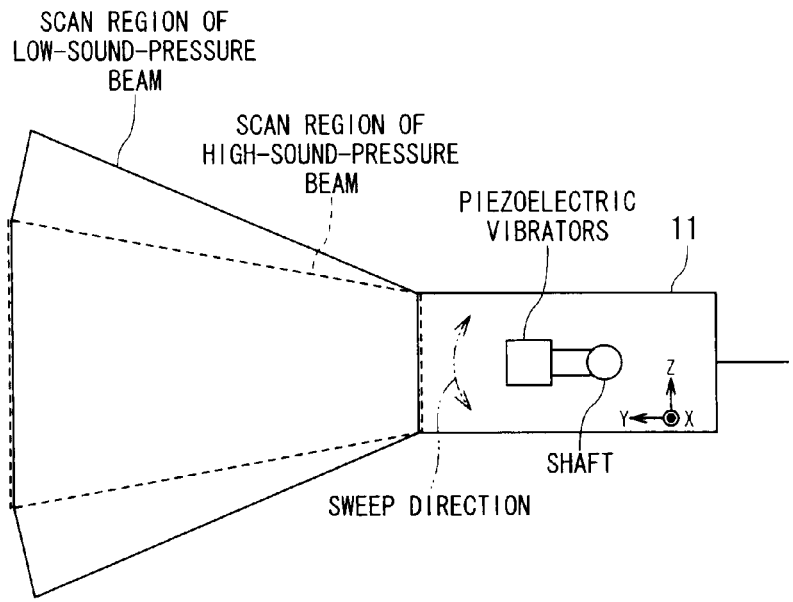
FIG. 8 is a schematic view showing a scan region of a low-sound-pressure beam and a scan region of a high-sound-pressure beam.

FIGS. 6 to 8 are schematic views showing the scan region of the low-sound-pressure beam and the scan region of the high-sound-pressure beam. Note that FIGS. 6 to 8 show the sweep direction component in the scan region of the low-sound-pressure beam and the sweep direction component in the scan region of the high-sound-pressure beam as examples of the scan region of the low-sound-pressure beam and the scan region of the high-sound-pressure beam.

It is known in a PR method in an ordinary two-dimensional scan that the status of a dyed image formed by the reflow of a bubble is different depending on a time during which the high-sound-pressure pulses are transmitted (accurately, the time passed after the contrast medium is injected). Further, since the status of the dyed image is also changed by the number of times of scan performed to the scan region, it is adjusted by optionally changing the time during which the high-sound-pressure pulses are transmitted and the number of times of scan of the high-sound-pressure pulses by the user. Since the scan region is expanded three-dimensionally, the scan region to which the high-sound-pressure pulses are transmitted is also newly added to one of the parameters relating to the dyed image, from which various variations can be considered. FIGS. 6 to 8 show examples thereof. These variations can be optionally selected by the user.

FIG. 6 shows a sweep direction component in the scan regions of the low-sound-pressure beam and the high-sound-pressure beam when the group of the piezoelectric vibrators disposed to the three-dimensional mechanical probe is swept about a shaft as a fulcrum, in which the sweep angle of the high-sound-pressure beam is the same as that of the low-sound-pressure beam. FIG. 7 shows the difference between the sweep direction component in the scan region of the low-sound-pressure beam and the sweep direction component in the scan region of the high-sound-pressure beam when the group of the piezoelectric vibrators, which is disposed to the three-dimensional mechanical probe, is swept, wherein the sweep angle of the high-sound-pressure beam is wider than that of the low-sound-pressure beam. Further, FIG. 8 the difference between the sweep direction component in the scan region of the low-sound-pressure beam and the sweep direction component in the scan region of the high-sound-pressure beam when the group of the piezoelectric vibrators, which is disposed to the three-dimensional mechanical probe, is swept, wherein the sweep angle of the high-sound-pressure beam is narrower than that of the low-sound-pressure beam.

Note that FIGS. 7 and 8 show the difference between the scan region of the low-sound-pressure beam and that of the high-sound-pressure beam in the sweep direction. However, the scan region of the low-sound-pressure beam may be different from that of the high-sound-pressure beam in the X-axis direction.

Figure 9:
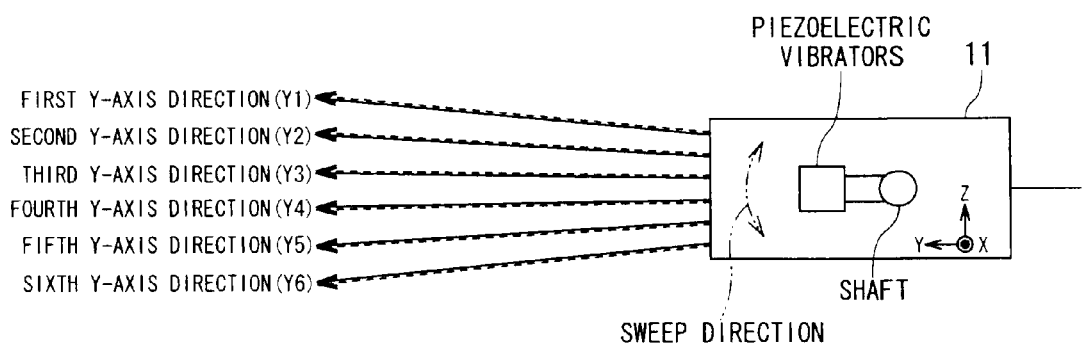
FIG. 9 is a view explaining a scan order of the low-sound-pressure beam and a scan order of the high-sound-pressure beam.
Figure 10:
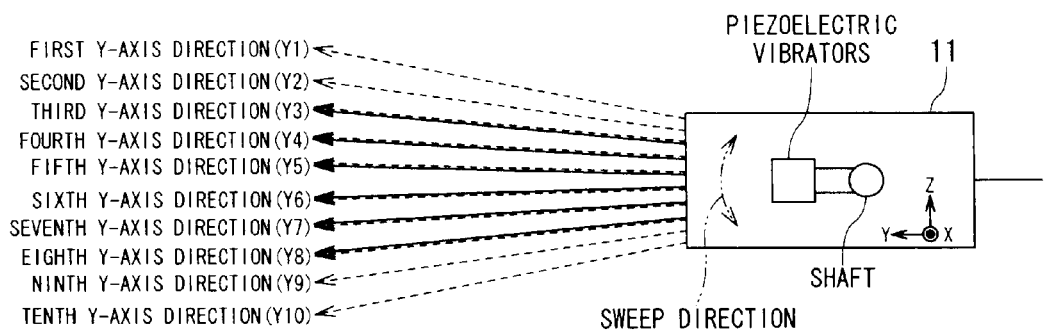
FIG. 10 is a view explaining a scan order of the low-sound-pressure beam and a scan order of the high-sound-pressure beam.
Figure 11:
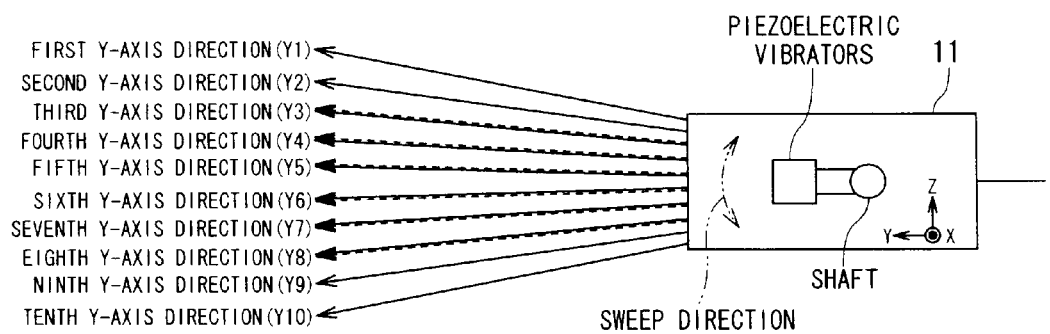
FIG. 11 is a view explaining a scan order of the low-sound-pressure beam and a scan order of the high-sound-pressure beam.

FIGS. 9 to 11 are views explaining the scan order of the low-sound-pressure beam and the scan order of the high-sound-pressure beam.

FIG. 9 shows an example of the sweep direction component in the scan region shown in FIG. 6. FIG. 10 shows an example of the sweep direction component in the scan region shown in FIG. 7. Further, FIG. 11 shows an example of the sweep direction component in the scan region shown in FIG. 8.

As shown in FIG. 9, planes, which are formed by the X-axis and respective Y-axis directions (a first Y-axis direction, a second Y-axis direction, . . . , a sixth Y-axis direction determined by the position of the group of the piezoelectric vibrators in the sweep direction), are scanned by sequentially transmitting the low-sound-pressure pulses while sweeping the group of the piezoelectric vibrators of the ultrasonic wave probe 11 in the scan region of the low-sound-pressure beam (shown in FIG. 6) under the control of the low-sound-pressure ultrasonic wave transmission/reception control unit 31. Specifically, first, an X-Y1 plane, which is formed by the X-axis direction and the first Y-axis direction (Y1), is scanned under the control of the low-sound-pressure ultrasonic wave transmission/reception control unit 31. The scan of the X-Y1 plane may be performed by receiving the echo on the X-Y1 plane in correspondence to the low-sound-pressure pulses transmitted a plurality of times (for example, transmission for dynamic focusing) or by receiving the echo on the X-Y1 plane in correspondence to the low-sound-pressure pulses transmitted once (for example, transmission for a parallel and simultaneous reception system).

Subsequently, as shown in FIG. 9, an X-Y2 plane, an X-Y3 plane, an X-Y4 plane, an X-Y5 plane, an X-Y6 plane, the X-Y6 plane, the X-Y5 plane, the X-Y4 plane, the X-Y3 plane, the X-Y2 plane, the X-Y1 plane, the X-Y1 plane, the X-Y2 plane, . . . , which are formed by the X-axis direction and the second Y-axis direction (Y2), are sequential scanned while sweeping the group of the piezoelectric vibrators in the scan region of the low-sound-pressure beam (shown in FIG. 6) under the control of the low-sound-pressure ultrasonic wave transmission/reception control unit 31. Note that the transmission of the low-sound-pressure pulses performed by the low-sound-pressure ultrasonic wave transmission/reception control unit 31 is not limited to the case that it is started from the X-Y1 plane (or X-Y6 plane) which is the outermost plane of the scan region of the low-sound-pressure beam.

Further, as shown in FIG. 9, the transmission of the low-sound-pressure pulse is stopped at arbitrary transmission timing while the low-sound-pressure pulses are being transmitted, and the high-sound pressure ultrasonic wave transmission unit 32 starts to transmit the high-sound pressure pulse. It is preferable for the high-sound pressure ultrasonic wave transmission unit 32 to start the transmission of the high-sound pressure pulse from, for example, the X-Y1 plane (or X-Y6 plane) which is the outermost surface of the scan region of the high sound pressure beam. Then, the X-Y2 plane, the X-Y3 plane, the X-Y4 plane, the X-Y5 plane, the X-Y6 plane, which are formed by the X-axis direction and the second Y-axis (Y2) direction, are sequentially scanned under the control of the high-sound pressure ultrasonic wave transmission unit 32 to thereby perform flash to the scan region of the high sound pressure beam. Note that the flash may be performed to the scan region of the high sound pressure beam only once or a plurality of times. Note that, in FIG. 9, explanation is made showing the "6" X-Y planes (X-Y1 plane to X-Y6 plane) for the purpose of convenience, the number of the planes is not limited to "6" and it is sufficient that the number of planes is "2" or more.

Further, as shown in FIG. 10, the plane, which is formed by the X-axis direction and the respective Y-axis directions (third Y-axis direction, fourth Y-axis direction, . . . , eighth Y-axis direction determined by the position of the group of the piezoelectric vibrators in the sweep direction), are scanned by sequentially transmitting the low-sound-pressure pulses while sweeping the group of the piezoelectric vibrators of the ultrasonic wave probe 11 in the scan region of the low-sound-pressure beam (shown in FIG. 7) under the control of the low-sound-pressure ultrasonic wave transmission/reception control unit 31. Specifically, first, the X-Y3 plane, which is formed by the X-axis direction and the third Y-axis direction (Y3) is scanned under the control of the low-sound-pressure ultrasonic wave transmission/reception control unit 31. The X-Y3 plane may be scanned by receiving the echo on the X-Y3 plane echo in correspondence to the low-sound-pressure pulses transmitted a plurality of times (for example, transmission for dynamic focusing) or by receiving the echo on the X-Y3 plane in correspondence to the low-sound-pressure pulses transmitted once (for example, transmission for parallel and simultaneous reception system).

Subsequently, the X-Y4 plane, the X-Y5 plane, the X-Y6 plane, an X-Y7 plane, an X-Y8 plane, the X-Y8 plane, the X-Y7 plane, the X-Y6 plane, the X-Y5 plane, the X-Y4 plane, the X-Y3 plane, the X-Y4 plane, . . . , which are formed by the X-axis direction and the fourth Y-axis direction (Y4), are sequentially scanned under the control of the low-sound-pressure ultrasonic wave transmission/reception control unit 31. Note that the transmission of the low-sound-pressure pulses by the low-sound-pressure ultrasonic wave transmission/reception control unit 31 is not limited to the case that it is started from the X-Y3 plane (or X-Y8 plane) which is the outermost plane of the scan region of the low-sound-pressure beam.

Further, as shown in FIG. 10, the transmission of the low-sound-pressure pulse is stopped at arbitrary transmission timing while the low-sound-pressure pulses are being transmitted, and the high-sound pressure ultrasonic wave transmission unit 32 starts to transmit the high-sound pressure pulse. It is preferable for the high-sound pressure ultrasonic wave transmission unit 32 to start the transmission of the high-sound pressure pulse from, for example, the X-Y1 plane (or X-Y10 plane) which is the outermost surface of the scan region of the high sound pressure beam. Then, the X-Y2 plane, the X-Y3 plane, the X-Y4 plane, the X-Y5 plane, the X-Y6 plane, the X-Y7 plane, the X-Y8 plane, an X-Y9 plane, an X-Y10 plane which are formed by the X-axis direction and the second Y-axis (Y2) direction, are sequentially scanned under the control of the high-sound pressure ultrasonic wave transmission unit 32 to thereby perform flash to the scan region of the high sound pressure beam. Note that the flash may be performed to the scan region of the high sound pressure beam only once or a plurality of times. Note that, in FIG. 10, explanation is made showing the "6" X-Y planes (X-Y3 plane to X-Y8 plane) for transmitting the low sound pulses and the "10" X-Y planes (X-Y1 plane to X-Y10 plane) for transmitting the high sound pulses for the purpose of convenience, the number of the planes is not limited to "6" and "10".

Further, as shown in FIG. 11, the plane, which is formed by the X-axis direction and the respective Y-axis directions (first Y-axis direction, second Y-axis direction, . . . , tenth Y-axis direction determined by the position of the group of the piezoelectric vibrators in the sweep direction), are scanned by sequentially transmitting the low-sound-pressure pulses while sweeping the group of the piezoelectric vibrators of the ultrasonic wave probe 11 in the scan region of the low-sound-pressure beam (shown in FIG. 8) under the control of the low-sound-pressure ultrasonic wave transmission/reception control unit 31. Specifically, first, the X-Y1 plane, which is formed by the X-axis direction and the first Y-axis direction (Y1) is scanned under the control of the low-sound-pressure ultrasonic wave transmission/reception control unit 31. The X-Y1 plane may be scanned by receiving the echo on the X-Y1 plane echo in correspondence to the low-sound-pressure pulses transmitted a plurality of times (for example, transmission for dynamic focusing) or by receiving the echo on the X-Y1 plane in correspondence to the low-sound-pressure pulses transmitted once (for example, transmission for parallel and simultaneous reception system).

Subsequently, the X-Y2 plane, the X-Y3 plane, the X-Y4 plane, the X-Y5 plane, the X-Y6 plane, the X-Y7 plane, the X-Y8 plane, the X-Y9 plane, the X-Y10 plane, X-Y10 plane, X-Y9 plane, the X-Y8 plane, the X-Y7 plane, the X-Y6 plane, the X-Y5 plane, the X-Y4 plane, the X-Y3 plane, the X-Y2 plane, the X-Y1 plane, the X-Y1 plane, the X-Y2 plane, . . . , which are formed by the X-axis direction and the second Y-axis direction (Y2), are sequentially scanned under the control of the low-sound-pressure ultrasonic wave transmission/reception control unit 31. Note that the transmission of the low-sound-pressure pulses by the low-sound-pressure ultrasonic wave transmission/reception control unit 31 is not limited to the case that it is started from the X-Y1 plane (or X-Y10 plane) which is the outermost plane of the scan region of the low-sound-pressure beam.

Further, as shown in FIG. 11, the transmission of the low-sound-pressure pulse is stopped at arbitrary transmission timing while the low-sound-pressure pulses are being transmitted, and the high-sound pressure ultrasonic wave transmission unit 32 starts to transmit the high-sound pressure pulse. It is preferable for the high-sound pressure ultrasonic wave transmission unit 32 to start the transmission of the high-sound pressure pulse from, for example, the X-Y3 plane (or X-Y8 plane) which is the outermost surface of the scan region of the high sound pressure beam. Then, the X-Y4 plane, the X-Y5 plane, the X-Y6 plane, the X-Y7 plane, and the X-Y8 plane, which are formed by the X-axis direction and the forth Y-axis (Y4) direction, are sequentially scanned under the control of the high-sound pressure ultrasonic wave transmission unit 32 to thereby perform flash to the scan region of the high sound pressure beam. Note that the flash may be performed to the scan region of the high sound pressure beam only once or a plurality of times. Note that, in FIG. 11, explanation is made showing the "10" X-Y planes (X-Y1 plane to X-Y10 plane) for transmitting the low sound pulses and the "6" X-Y planes (X-Y3 plane to X-Y8 plane) for transmitting the high sound pulses for the purpose of convenience, the number of the planes is not limited to "10" and "6".

Further, the volume data generation unit 33 shown in FIG. 3 has a function for generating (reconstructing) volume data by three-dimensionally rearranging a scan line signal train obtained by scanning the ultrasonic wave based on the image data of the ultrasonic wave stored in the image memory 25.

The three-dimensional display processing unit 34 has a function for performing a rendering process for two-dimensionally displaying the image data of the three-dimensional ultrasonic image based on the volume data generated by the volume data generation unit 33. The image data after the rendering process is performed is displayed on the monitor 13 through the display control unit 24.

Figure 12:
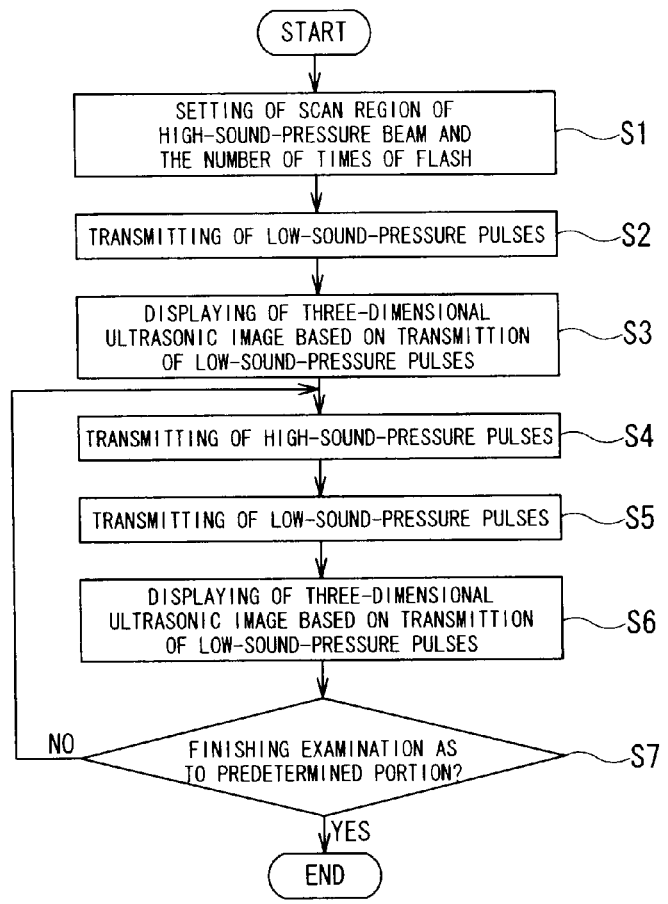
FIG. 12 is a flowchart showing an operation of the ultrasonic diagnostic apparatus.

Subsequently, an operation of the ultrasonic diagnostic apparatus 10 will be explained using a flowchart shown in FIG. 12.

The ultrasonic diagnostic apparatus 10 is operated according to steps S1 to S7 by that the CPU 26 executes a program, thereby a clinical examination is performed by the ultrasonic diagnostic apparatus 10.

First, the scan region of the high-sound-pressure beam and the number of times of flash are set (step S1). For example, the scan region of the high-sound-pressure beam and the number of times of flash are manually set by the user using the operation panel 14.

Figure 13:
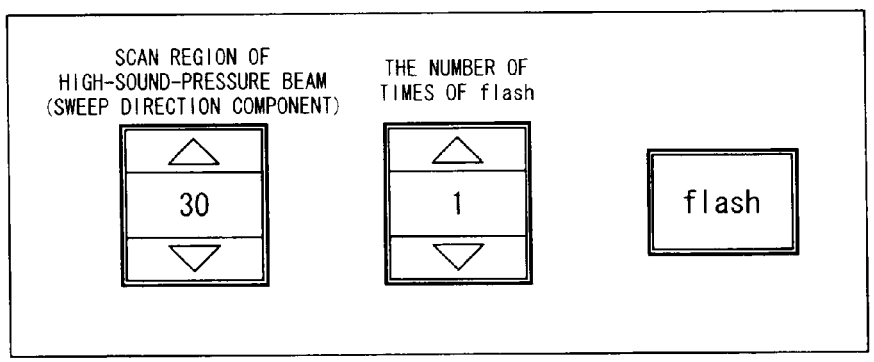
FIG. 13 is a view showing an example of an input screen of the scan region of the high-sound-pressure beam and the number of times of flash.

FIG. 13 is a view showing an example of an input screen of the scan region of the high-sound-pressure beam and the number of times of flash. Note that FIG. 13 shows a screen to which only a sweep direction component in the scan region of the high-sound-pressure beam can be input as an example of the scan region of the high-sound-pressure beam.

As shown in FIG. 13, the scan region of the high-sound-pressure beam and the number of times of flash can be input through the input screen displayed on the operation panel 14. Further, the user can change the scan region of the high-sound-pressure beam and the number of times of flash through the input screen shown in FIG. 13 while observing the three-dimensional ultrasonic image displayed at step S3 or S6 during the clinical examination.

Next, the contrast medium is injected into the body of the patient P. The contrast medium injected into the body of the patient P issues a harmonic signal without being broken even if the low-sound-pressure ultrasonic wave is transmitted and can form an image for a long time.

Next, the transmission unit of the transmission/reception unit 21 scans the X-Y plane, which is formed by the X-axis direction and the Y-axis direction that is determined by the position of the ultrasonic vibrator in the sweep direction (for example, the first Y-axis direction (Y1) shown in FIG. 9, the third Y-axis direction (Y3) shown in FIG. 10, or the first Y-axis direction (Y1) shown in FIG. 11) by an arbitrary PRP by transmitting the low-sound-pressure pulses from the ultrasonic wave probe 11 by which the contrast agent bubble is not relatively broken. The X-Y plane may be scanned by receiving the echo on the X-Y plane echo in correspondence to the low-sound-pressure pulses transmitted a plurality of times (for example, transmission for dynamic focusing) or by receiving the echo on the X-Y plane in correspondence to the low-sound-pressure pulses transmitted once (for example, transmission for parallel and simultaneous reception system).

Further, the low-sound-pressure pulses are sequentially transmitted to a plurality of the X-Y planes formed by the X-axis and a plurality of Y-axis directions while sweeping the group of the piezoelectric vibrators disposed to the three-dimensional mechanical probe as the ultrasonic wave probe 11 (step S2).

The transmission of the low-sound-pressure pulses at step S2 causes the reception unit of the transmission/reception unit 21 to form the integral beams of transmission and reception of the ultrasonic wave by reception directionality and transmission directionality. The B mode processing unit 22a performs the logarithm amplification process, the envelope detection process, and the like to the echo signal output from the reception unit of the transmission/reception unit 21, and generates the data in which signal intensity is expressed by the brightness of luminance. The image generation unit 23 converts the scan line signal train obtained by scanning the ultrasonic wave into a scan line signal train of an ordinary video format represented by TV and the like, and generates the image data of an ultrasonic image as a display image, and stores the image data in the image memory 25. Next, the volume data is generated by three-dimensionally rearranging the scan line signal train obtained by scanning the ultrasonic wave based on the image data of the ultrasonic wave stored in the image memory 25. Next, the rendering process is performed to two-dimensionally display the image data of the three-dimensional ultrasonic image based on the volume data, and the image data after the rendering process is performed is displayed on the monitor 13 through the display control unit 24 (step S3).

Next, the transmission of the low-sound-pressure pulses is stopped at the timing when a flash button displayed on the input screen shown in FIG. 13 is depressed, and the high-sound-pressure pulses start to be transmitted by a PRP smaller than that of the low-sound-pressure pulses in the scan region of the high-sound-pressure pulses set at step S1 and by the number of times of flash. It is preferable to start the transmission of the high-sound-pressure pulses from the X-Y plane (for example, first Y-axis direction (Y1) shown in FIG. 9, first Y-axis direction (Y1) shown in FIG. 10, or third Y-axis direction (Y3) shown in FIG. 11) which is the outermost surface of the scan region.

Further, to perform flash in the scan region of the high-sound-pressure beam, the high-sound-pressure pulses are sequentially transmitted to a plurality of X-Y planes formed by the X-axis and a plurality of Y-axis directions while sweeping the group of the piezoelectric vibrators disposed to the three-dimensional mechanical probe as the ultrasonic wave probe 11 (step S4). Note that the high-sound-pressure pulses may be flashed to the scan region of the high-sound-pressure beam at step S4 only once or a plurality of times according to the number of times of flash set at step S1.

When the transmission of the high-sound-pressure pulses is finished at step S4 according to the scan region of the high-sound-pressure beam and the number of times of flash set at step S1, the transmission/reception unit 21 scans the X-Y plane, which is formed by the X-axis direction and the Y-axis direction that is determined by the position of the group of the piezoelectric vibrators in the sweep direction, by causing the low-sound-pressure pulses to be transmitted from the ultrasonic wave probe 11 by an arbitrary PRP likewise step S2. Further, to scan the scan region of the low-sound-pressure beam in its entirety, the low-sound-pressure pulses are sequentially transmitted to a plurality of X-Y planes formed by the X-axis and a plurality of Y-axis directions while sweeping the group of the piezoelectric vibrators disposed to the three-dimensional mechanical probe as the ultrasonic wave probe 11 (step S5).

When the low-sound-pressure pulses are transmitted at step S5, the reception unit of the transmission/reception unit 21 forms the integral beams of the transmission and reception of the ultrasonic wave by the reception directionality and the transmission directionality. Next, the B mode processing unit 22a performs the logarithm amplification process, the envelope detection process, and the like to the echo signal output from the reception unit of the transmission/reception unit 21, and generates the data in which signal intensity is expressed by the brightness of luminance. The image generation unit 23 converts the scan line signal train obtained by scanning the ultrasonic wave into a scan line signal train of an ordinary video format represented by TV and the like, and generates the image data of an ultrasonic image as a display image, and stores the image data in the image memory 25. Next, the volume data is generated by three-dimensionally rearranging the scan line signal train obtained by scanning the ultrasonic wave based on the image data of the ultrasonic wave stored in the image memory 25. Next, the rendering process is performed to two-dimensionally display the image data of the three-dimensional ultrasonic image based on the volume data, and the image data after the rendering process is performed is displayed on the monitor 13 through the display control unit 24 (step S6).

Next, whether or not the clinical examination as to a predetermined portion of the patient P is finished is assessed (step S7). When it is assessed YES at step S7, that is, when it is determined that the clinical examination as to the predetermined portion of the patient P is finished, the transmission of the low-sound-pressure pulses is stopped, and the clinical examination is finished.

In contrast, when it is assessed NO at step S7, that is, when it is determined that the clinical examination as to the predetermined portion of the patient P is not finished, the low-sound-pressure pulses are continuously transmitted at step S5. Next, the transmission of the low-sound-pressure pulses is stopped at the timing when the flash button displayed on the input screen shown in FIG. 13 is depressed, and the high-sound-pressure pulses start to be transmitted by a PRP smaller than that of the low-sound-pressure pulses in the scan region of the high-sound-pressure beam set at S1 and by the number of times of flash (step S4).

Figure 14:
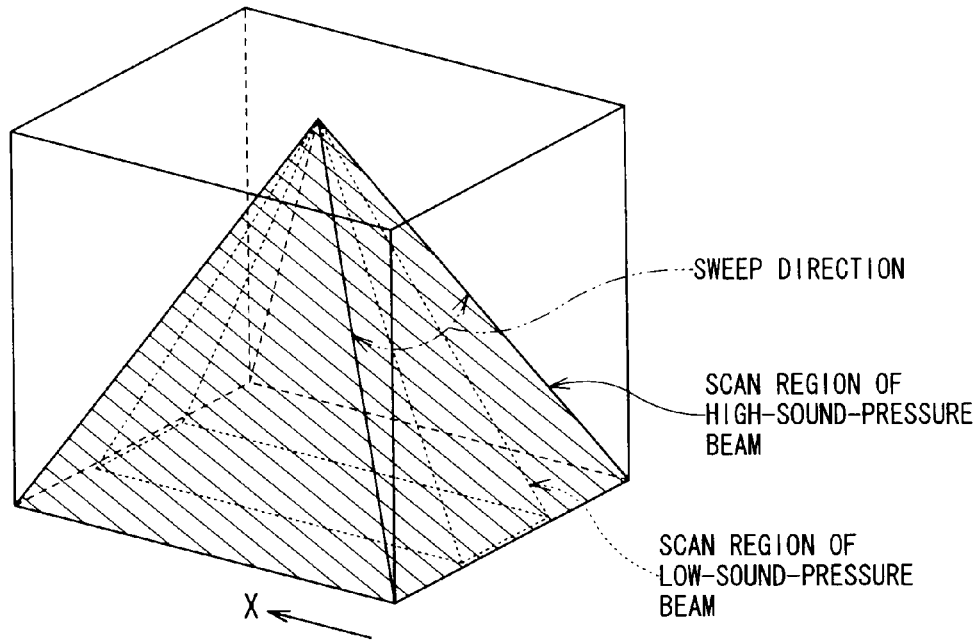
FIG. 14 is a view showing an example of three-dimensional indicators in the scan region of the low-sound-pressure beam and the high-sound-pressure beam.
Figure 15:
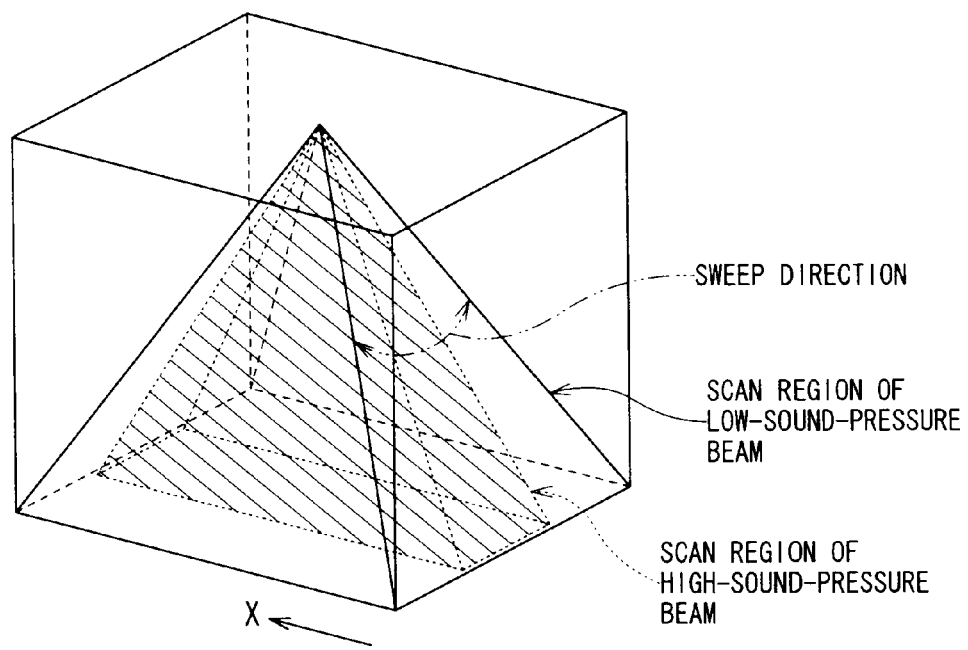
FIG. 15 is a view showing an example of three-dimensional indicators in the scan region of the low-sound-pressure beam and the high-sound-pressure beam.

FIGS. 14 and 15 are views showing an example of three-dimensional indicators in the scan regions of the low-sound-pressure beam and the high-sound-pressure beam. FIG. 14 shows the example of the three-dimensional indicator in the scan region shown in FIG. 7, whereas FIG. 15 shows the example of the three-dimensional indicator in the scan region shown in FIG. 8.

To simply find the scan regions in the low-sound-pressure beam and the high-sound-pressure beam while the user performs the clinical examination at step S1 to S7, the high-sound-pressure ultrasonic wave transmission unit 32 displays the three-dimensional indicators of scan regions in the low-sound-pressure beam and the high-sound-pressure beam on the monitor 13. Here, it is preferable that the three-dimensional indicators displayed as shown in FIGS. 14 and 15 be formed such that the difference between the scan regions of the low-sound-pressure beam which are displayed in an overlapped state and the scan regions of the high-sound-pressure beam which are displayed likewise can be visually recognized simply by the user. For example, in the three-dimensional indicator shown in FIGS. 14 and 15, only the scan region in the high-sound-pressure beam is completely colored.

Note that, as explained in FIGS. 7 and 8, FIGS. 14 and 15 show the three-dimensional indicators in which only the sweep direction components in the scan regions are different from each other, three-dimensional indicators, in which the X-axis direction components in the scan regions are also different from each other in addition to the sweep direction components, may be employed. Further, three-dimensional indicators, in which only the X-axis direction components in the scan regions are different from each other, may be employed.

According to the ultrasonic diagnostic apparatus 10 of the embodiment, it is possible to three-dimensionally observe the behavior of the reflow of the contrast agent bubble by the display at step S6. Further, according to the ultrasonic diagnostic apparatus 10 of the embodiment, since the scan region of the high-sound-pressure beam can be simply changed, it is possible to cope with a severe request to the scan region of the high-sound-pressure beam from the user. Therefore, the ultrasonic diagnostic apparatus 10 of the embodiment can provide the image information of the reflow of a contrast agent bubble desired by the user.

What is claimed is:

1. An ultrasonic diagnostic apparatus, comprising:
    an ultrasonic wave probe configured to transmit low-sound-pressure pulses and high-sound-pressure pulses having a different sound pressure to a scan region formed so as to include a predetermined portion of an object to which a contrast agent bubble is injected, and to receive an echo corresponding to the low-sound-pressure pulses;
    a low-sound-pressure ultrasonic wave transmission/reception control unit configured to control the ultrasonic wave probe to transmit the low-sound-pressure pulses to the scan region at a first pulse repetition period, and to control the ultrasonic wave probe to receive the echo corresponding to the low-sound-pressure pulses;
    a high-sound-pressure ultrasonic wave transmission control unit configured to control the ultrasonic wave probe to transmit the high-sound-pressure pulses to the scan region at a second pulse repetition period shorter than the first pulse repetition period;
    a switching control unit configured to control the low-sound-pressure ultrasonic wave transmission/reception control unit and the high-sound-pressure ultrasonic wave transmission control unit so that the transmission of the low-sound-pressure pulses and the transmission of the high-sound-pressure pulses are alternately switched; and
    a display control unit configured to control display of ultrasonic image data based on the echo corresponding to the low-sound-pressure pulses on a monitor,
    wherein the ultrasonic wave probe is a three-dimensional mechanical probe for mechanically sweeping transducers disposed one-dimensionally, and the high-sound-pressure ultrasonic wave transmission control unit controls a sweep speed of the transducers so as to be faster when transmitting the high-sound-pressure pulses than when transmitting the low-sound-pressure pulses.

2. The ultrasonic diagnostic apparatus according to claim 1, wherein the high-sound-pressure ultrasonic wave transmission control unit makes a first sweep angle of the transducers when the high-sound-pressure pulses are transmitted different from a second sweep angle of the transducers when the low-sound-pressure pulses are transmitted.

3. The ultrasonic diagnostic apparatus according to claim 2, further comprising:
    an operation panel configured to input the first sweep angle of the high-sound-pressure pulses to the high-sound-pressure ultrasonic wave transmission control unit.

4. The ultrasonic diagnostic apparatus according to claim 1, wherein the high-sound-pressure ultrasonic wave transmission control unit is configured to make at least part of a first scan region of a high-sound-pressure beam formed by the high-sound-pressure pulses overlapping with a second scan region of a low-sound-pressure beam formed by the low-sound-pressure pulses.

5. The ultrasonic diagnostic apparatus according to claim 4, wherein the high-sound-pressure ultrasonic wave transmission control unit is configured to display the scan region of the low-sound-pressure beam formed by the low-sound-pressure pulses and the scan region of the high-sound-pressure beam formed by the high-sound-pressure pulses as visually recognizable indicators on the monitor.

6. The ultrasonic diagnostic apparatus according to claim 1, wherein the high-sound-pressure ultrasonic wave transmission control unit is configured to execute flash a plurality of times so that the high-sound-pressure pulses are repeatedly transmitted to the scan region of the high-sound-pressure beam formed by the high-sound-pressure pulses.

7. The ultrasonic diagnostic apparatus according to claim 6, further comprising:
    an operation panel configured to input a number of times of the flash to the high-sound-pressure ultrasonic wave transmission control unit.

8. The ultrasonic diagnostic apparatus according to claim 1, wherein the ultrasonic wave probe further comprises a temperature measurement unit configured to measure a temperature of transducers of the ultrasonic wave probe in a time zone in which the high-sound-pressure pulses are transmitted, wherein when the temperature measured by the temperature measurement unit exceeds a threshold value, the high-sound-pressure ultrasonic wave transmission control unit controls the ultrasonic wave probe so that the transmission of the high-sound-pressure pulses is finished.

9. An ultrasonic diagnostic method, comprising:
    a high-sound-pressure ultrasonic wave transmission control step of controlling an ultrasonic wave probe to transmit high-sound-pressure pulses to a scan region at a first pulse repetition period shorter than a second pulse repetition period;

a low-sound-pressure ultrasonic wave transmission/reception control step of controlling the ultrasonic wave probe to transmit low-sound-pressure pulses to the scan region at the second pulse repetition period, and controlling the ultrasonic wave probe to receive an echo corresponding to the low-sound-pressure pulses, alternately switching the transmission of the low-sound-pressure pulses and the transmission of the high-sound-pressure pulses; and controlling display of ultrasonic image data based on the echo corresponding to the low-sound-pressure pulses on a monitor, wherein the ultrasonic wave probe is a three-dimensional mechanical probe for mechanically sweeping transducers disposed one-dimensionally, and the high-sound-pressure ultrasonic wave transmission control step includes controlling a sweep speed of the transducers so as to be faster when transmitting the high-sound-pressure pulses than when transmitting the low-sound-pressure pulses.

10. The ultrasonic diagnostic method according to claim 9, wherein the high-sound-pressure ultrasonic wave transmission control step includes making a first sweep angle of the transducers when the high-sound-pressure pulses are transmitted different from a second sweep angle of the transducers when the low-sound-pressure pulses are transmitted.

11. The ultrasonic diagnostic method according to claim 9, wherein the high-sound-pressure ultrasonic wave transmission control step includes making at least part of a first scan region of a high-sound-pressure beam formed by the high-sound-pressure pulses overlap with a second scan region of a low-sound-pressure beam formed by the low-sound-pressure pulses.

12. The ultrasonic diagnostic method according to claim 11, wherein the high-sound-pressure ultrasonic wave transmission control step includes displaying the scan region of the low-sound-pressure beam formed by the low-sound-pressure pulses and the scan region of the high-sound-pressure beam formed by the high-sound-pressure pulses as visually recognizable indicators on the monitor.

13. The ultrasonic diagnostic method according to claim 9, wherein the high-sound-pressure ultrasonic wave transmission control step includes executing flash a plurality of times so that the high-sound-pressure pulses are repeatedly transmitted to the scan region of a high-sound-pressure beam formed by the high-sound-pressure pulses.

14. The ultrasonic diagnostic method according to claim 9, wherein the high-sound-pressure ultrasonic wave transmission control step includes controlling the ultrasonic wave probe so that the transmission of the high-sound-pressure pulses is finished, when a temperature of transducers of the ultrasonic wave probe in a time zone in which the high-sound-pressure pulses are transmitted exceeds a threshold value.

15. The ultrasonic diagnostic apparatus according to claim 1, further comprising:

a volume data generation unit configured to generate volume data based on the echo received by the ultrasonic wave probe under the control of the low-sound-pressure ultrasonic wave transmission/reception control unit; and a three-dimensional display processing unit configured to generate three-dimensional image data by performing a rendering process on a basis of the volume data, wherein the display control unit is configured to control display of the three-dimensional image data as the ultrasonic image data on the monitor.

16. The ultrasonic diagnostic method according to claim 9, further comprising:

generating volume data based on the echo received by the ultrasonic wave probe under the control of the low-sound-pressure ultrasonic wave transmission/reception control step; and generating three-dimensional image data by performing a rendering process on a basis of the volume data, wherein the controlling controls display of the three-dimensional image data as the ultrasonic image data on the monitor.

\* \* \* \* \*